US010800586B2

(12) United States Patent
Voth et al.

(10) Patent No.: US 10,800,586 B2
(45) Date of Patent: Oct. 13, 2020

(54) APPARATUS AND METHOD FOR DETERRING PETS FROM MEDICATION CONTAINERS

(71) Applicants: Eric Jon Voth, Maplewood, MN (US); Jason Andrew Voth, Maplewood, MN (US); Joseph William Nelson, Hugo, MN (US); Christopher Ronald Nelson, Hugo, MN (US); Justin Yong Lim, North Oaks, MN (US); Karis Yong Hee Lim, North Oaks, MN (US); Andrew Nicholas Dillner, White Bear Lake, MN (US); Norah Elizabeth Dillner, White Bear Lake, MN (US); Scott Eric Simenson, River Falls, WI (US)

(72) Inventors: Eric Jon Voth, Maplewood, MN (US); Jason Andrew Voth, Maplewood, MN (US); Joseph William Nelson, Hugo, MN (US); Christopher Ronald Nelson, Hugo, MN (US); Justin Yong Lim, North Oaks, MN (US); Karis Yong Hee Lim, North Oaks, MN (US); Andrew Nicholas Dillner, White Bear Lake, MN (US); Norah Elizabeth Dillner, White Bear Lake, MN (US); Scott Eric Simenson, River Falls, WI (US)

( * ) Notice: Subject to any disclaimer, the term of this patent is extended or adjusted under 35 U.S.C. 154(b) by 451 days.

(21) Appl. No.: 15/875,662

(22) Filed: Jan. 19, 2018

(65) Prior Publication Data
US 2018/0208373 A1    Jul. 26, 2018

Related U.S. Application Data

(60) Provisional application No. 62/449,504, filed on Jan. 23, 2017.

(51) Int. Cl.
*B65D 55/02*  (2006.01)
*B65D 23/08*  (2006.01)
*G16H 20/10*  (2018.01)

(52) U.S. Cl.
CPC ............. *B65D 55/02* (2013.01); *B65D 23/08* (2013.01); *B65D 2203/12* (2013.01); *B65D 2401/00* (2020.05); *G16H 20/10* (2018.01)

(58) Field of Classification Search
CPC .... B65D 55/02; B65D 23/08; B65D 2401/00; B65D 2203/12; G16H 20/10
See application file for complete search history.

(56) References Cited

U.S. PATENT DOCUMENTS 4,153,009 A * 5/1979 Boyle ...................... A61D 9/00
                                                                  119/850
4,711,368 A * 12/1987 Simons ................ B65D 55/028
                                                                  116/100

(Continued)

*Primary Examiner* — Nimeshkumar D Patel
*Assistant Examiner* — Tania Courson

(57) ABSTRACT

The present invention provides a method and apparatus for deterring pets or other animals from biting or chewing into medication containers. In some embodiments, the invention consists of two or more conductive metal sheets or strips in layers around the side of the container, which are wired to complete a circuit when pressed by the force of an animal's bite or touched by an animal's tongue. In some embodiments, the sheets or strips are spaced or held apart so that a normal human grip would not have sufficient force to complete the circuit. In some embodiments, the device slides onto the medication container with a friction fit, and is removable for use on future containers. In some embodiments, the circuit includes a battery-powered alarm to deter the animal. In other embodiments, the circuit delivers a mild electrical shock to the animal's mouth or tongue through the metal strips or sheets.

19 Claims, 3 Drawing Sheets

(56) References Cited

U.S. PATENT DOCUMENTS

| | | | | |
|---|---|---|---|---|
| 4,969,418 A * | 11/1990 | Jones | ............... | A01K 15/023 119/712 |
| 5,896,830 A * | 4/1999 | Stampe | ............... | A01K 13/00 119/822 |
| 6,314,914 B1 * | 11/2001 | Betzen | ............... | A01M 29/06 119/712 |
| 6,925,748 B2 * | 8/2005 | McGill | ............... | A01M 29/26 43/98 |
| 7,170,409 B2 * | 1/2007 | Ehrensvard | ...... | G06K 19/07798 340/539.13 |
| 7,219,627 B1 * | 5/2007 | Egloff | ............... | A01K 15/02 119/859 |
| 7,835,132 B2 * | 11/2010 | Mesika | ............... | H05C 1/00 361/223 |
| 8,061,307 B2 * | 11/2011 | Minick | ............... | A01K 15/02 119/822 |
| 8,081,065 B2 * | 12/2011 | Martetschlager | ....... | H02S 50/00 119/428 |
| 8,578,891 B2 * | 11/2013 | Vickery | ............... | A01K 13/006 119/850 |
| 8,695,538 B2 * | 4/2014 | Pitzen | ............... | A01K 15/029 119/859 |
| 9,621,974 B2 * | 4/2017 | Mohindra | ............ | B65D 55/028 |
| 2002/0067264 A1 * | 6/2002 | Soehnlen | ......... | G06K 19/07749 340/572.1 |
| 2003/0058740 A1 * | 3/2003 | Jincks | ............... | A01M 31/002 367/139 |
| 2004/0169585 A1 * | 9/2004 | Smith | ............... | A01M 29/10 340/384.2 |
| 2007/0268687 A1 * | 11/2007 | Scannell, Jr. | ........... | F21S 6/002 362/154 |
| 2009/0188443 A1 * | 7/2009 | Minick | ............... | A61D 9/00 119/822 |
| 2009/0272336 A1 * | 11/2009 | Cooke, Jr. | ............... | A61D 9/00 119/850 |
| 2011/0148651 A1 * | 6/2011 | Hendrickson | ........... | D06F 33/00 340/686.6 |
| 2011/0181410 A1 * | 7/2011 | Levinson | ............... | G16H 40/67 340/540 |
| 2015/0334991 A1 * | 11/2015 | Foley | ............... | A01K 27/009 119/720 |
| 2016/0306932 A1 * | 10/2016 | Fateh | ............... | G06F 3/014 |
| 2017/0173262 A1 * | 6/2017 | Veltz | ............... | A61B 5/0022 |

* cited by examiner

APPARATUS AND METHOD FOR DETERRING PETS FROM MEDICATION CONTAINERS

CROSS-REFERENCE TO RELATED APPLICATIONS

This application claims the benefit of U.S. Provisional Patent Application No. 62/449,504, filed Jan. 23, 2017, the contents of which are hereby incorporated by reference herein in their entirety.

FIELD OF THE INVENTION

This invention relates to the field of electric alarms, and more specifically to a method and apparatus of preventing pets or other animals from biting or chewing open any kind of pill bottle or other medication container.

BACKGROUND OF THE INVENTION

Many human medications can be harmful or even fatal if ingested by pets. Child-resistant pill bottles and medication containers have been patented since at least 1978. Marshall, et al. (U.S. Pat. No. 4,069,942, which is incorporated herein by reference) describes a closure lid with rotation-resistant engagement provided by radially-inwardly directed ratchet teeth. But pill bottles are almost always made of plastic, and even child-resistant caps cannot resist the bite force of canines or other pets. Extremely thick or strong plastic would not be cost-effective, or feasible, because transparency is desired. Metal or other strong materials for the cap and bottle may not be feasible for this reason also.

SUMMARY OF THE INVENTION

The present invention provides a method and apparatus for deterring pets or other animals from biting or chewing into medication containers. A pressure sensor around the side of the container completes a circuit when pressed by the force of an animal's bite or touched by an animal's tongue. The circuit includes a battery-powered alarm to scare or deter the animal. It could also deliver a mild electrical shock to the animal's mouth or tongue, when the pressure sensor consists of conductive metal strips or sheets. The pressure sensor is calibrated (or the sheets or strips are spaced or held apart) so that a normal human grip does not have sufficient force to complete the circuit, and the entire device can slide onto the medication container with a friction fit. The invention can be manufactured in different sizes and shapes to fit on many different standard medication containers. The invention can be connected to the Internet of Things, to alert the medication owner when the alarm is triggered.

DESCRIPTION OF PREFERRED EMBODIMENTS

Although the following detailed description contains many specifics for the purpose of illustration, a person of ordinary skill in the art will appreciate that many variations and alterations to the following details are within the scope of the invention. Specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The embodiments shown in the Figures and described here may include features that are not included in all specific embodiments. A particular embodiment may include only a subset of all of the features described, or a particular embodiment may include all of the features described.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Figure 1:
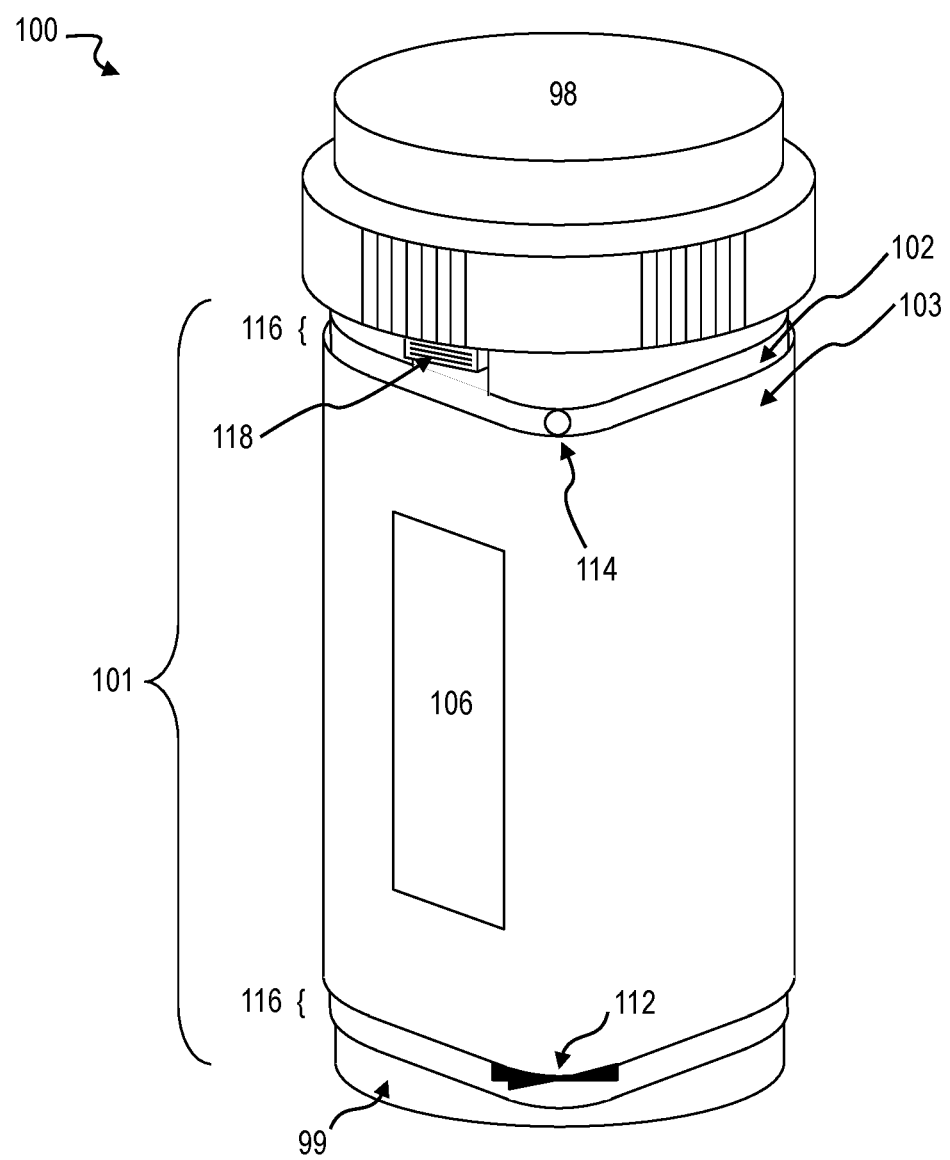
FIG. 1 is a perspective view of medication container system 100 that shows one embodiment of the present invention, fitting onto a standard round pill bottle 99 with cap 98, wherein the alarm sleeve apparatus 101 has a pair of thinly spaced metal sheets 102, 103 that complete a circuit when they are pressed together by an animal's bite or their edges are simultaneously touched by an animal's saliva or moist tongue.
Figure 2:
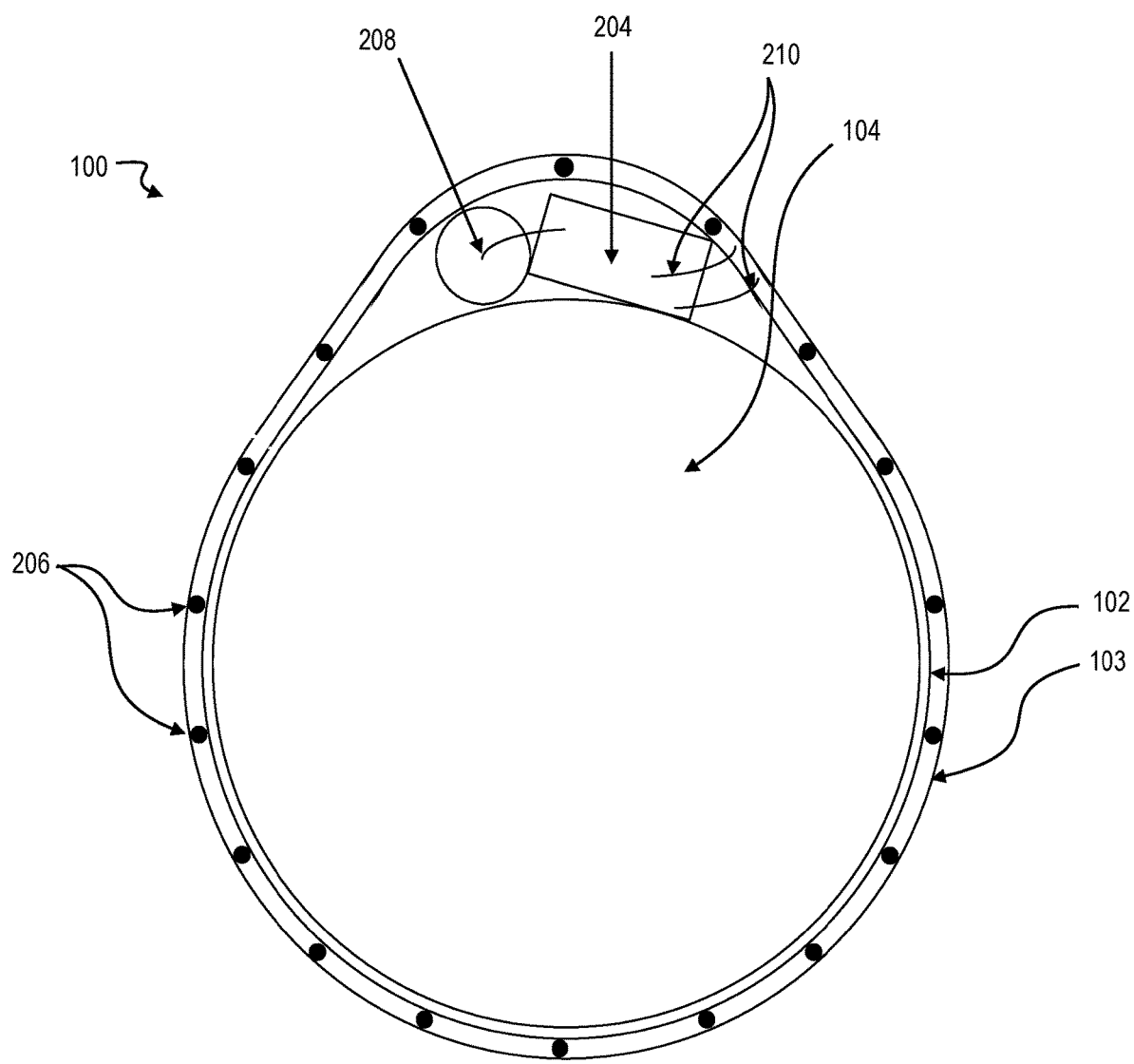
FIG. 2 is a bottom view of medication container system 100 that shows the two metal sheets or strips 102 and 103, and how they protect the batteries 208 and sensitive alarm circuitry 204 underneath from the force of an animal's bite.

FIG. 1 is a perspective view of medication container system 100 that shows one embodiment of the present invention, fitting onto a standard round pill bottle 99, wherein the alarm sleeve apparatus 101 has a pressure sensor that complete a circuit under the force of an animal's bite. Referring initially to FIG. 1, the invention apparatus 101 is shown comprising two conductive metal sheets 102 and 103 in concentric or coaxial layers around the side of the medication container 99, said sheets or strips being wired internally to complete a circuit when pressed together by the force of an animal's bite or when their edges are touched by an animal's tongue (saliva completing the circuit). In some embodiments, completing the circuit activates alarm circuitry 204 (in FIG. 2, the bottom view). Said alarm can comprise a standard resistor-capacitor (RC) oscillating circuit with one or more piezoelectric elements, as is well known in the art. The alarm circuitry is connected to the conductive metal sheets 102 and 103 with wires 210. In some embodiments, the alarm unit activates with a sound greater than 80 decibels (dB); in other embodiments, the sound level is less than 80 dB.

In other embodiments, the circuitry 204 uses one or more batteries 208 to deliver a mild electrical shock to the animal's mouth or tongue through the conductive metal strips or sheets.

In some embodiments, the conductive sheets or strips 102, 103 are held apart by spacers 206 so that a normal human grip has insufficient force to complete the circuit. In some embodiments, the spacing is accomplished by interposing one or more spacers 206 that include tiny beads or pieces of plastic, Styrofoam® or other expanded foam between metal sheets 102 and 103; in other embodiments, one or more spacers 206 that include fabric netting of the proper thickness (for example, in some embodiments, 0.5 mm to 1.5 mm) and spacing (for example, in some embodiments, 0.5 cm to 1.5 cm) is used between metal sheets 102 and 103; in yet other embodiments, the one or more spacers 206 include dabs of glue or adhesive, or other spacing objects or material, without limitation.

In some other embodiments, a single pressure-sensing sheet or membrane with two terminals is used to complete the circuit. Said sheets or membranes are known in the art, and can be manufactured so that a normal human grip has insufficient force to complete the circuit.

In some embodiments, the entire alarm sleeve apparatus 101 slides onto the medication container 99 with a friction fit, and is removable for use on other containers.

In some embodiments, the label for the patient's medication is affixed around the entire circumference of the apparatus 101, as pharmacists are accustomed to do in normal practice. A duplicate label may also be attached to the container 99 itself, underneath the apparatus, for safety of labeling in case the apparatus slides off or becomes dislodged.

In some embodiments, a switch 112 arms or disarms the entire apparatus to prevent accidental loss of battery power when the device is not in use. In such embodiments, the switch is of a type (rocker, pushbutton, etc.) and is positioned in such a way that an animal's bite could not easily turn it on or off.

In some embodiments, the invention contains an indicator light 114, possibly intermittent like that of a smoke alarm, to confirm to the medication owner that the device is activated and working.

In other embodiments, the indicator light flashes to warn of low battery power.

In yet other embodiments, the alarm chirps to warn of low battery power.

Figure 3:
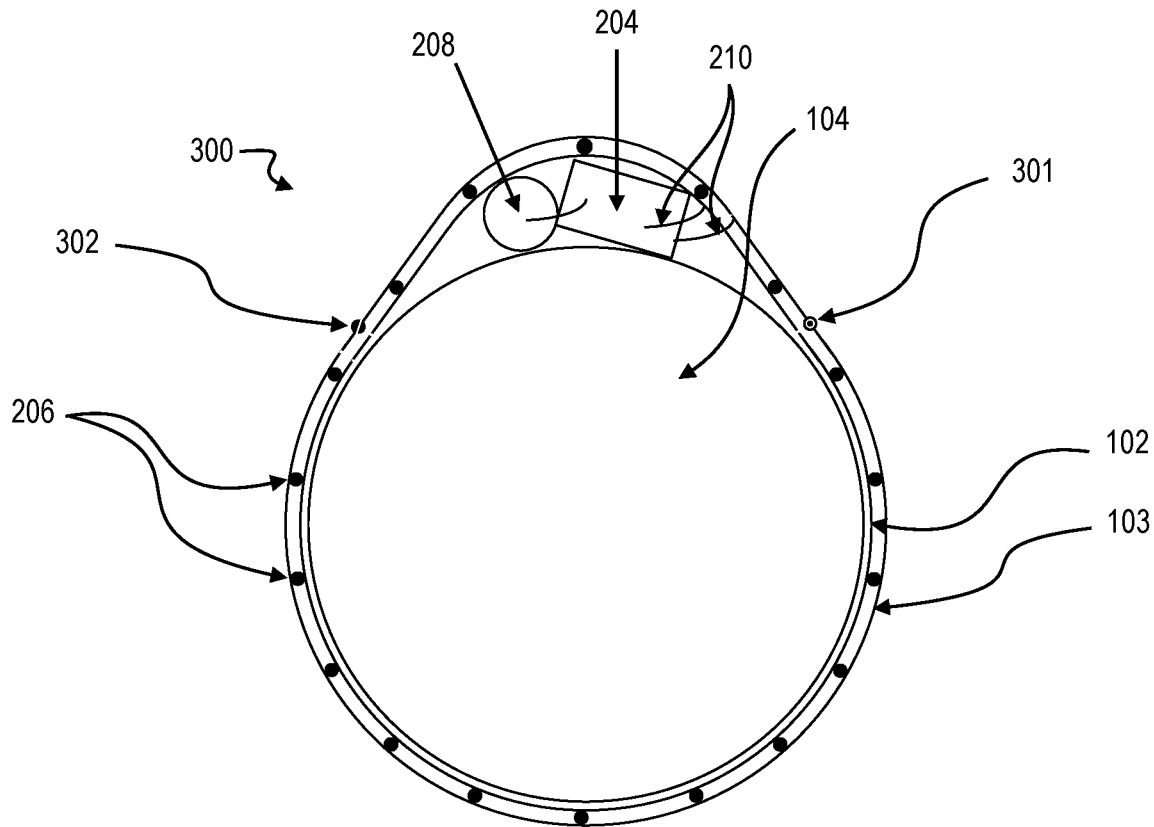
FIG. 3 is a bottom view showing an alternate embodiment—medication container system 300 using a hinge 301 and clasp 302.

In some embodiments (FIG. 3), the invention has a hinge 301 and a clasp 302 to allow easier access to change the batteries 208. In other embodiments, a battery access door 106 is on the outside of the apparatus, and the outer and/or inner conductive sheet is not present there.

In some embodiments, lateral gaps 116 between the edges of the inner and outer conductive sheets increase the likelihood of the animal's tongue completing the circuit even without a physical bite. (In some embodiments, current limiting on the shock unit is included to prevent harm to animal, while still providing an aversive stimulus to prevent recurring biting.)

In an alternative embodiment, a locking mechanism 118 helps to prevent the device from being accidentally or even deliberately removed from the medication container 99. In different embodiments, the locking mechanism is a snap, a latch, an adhesive patch, or other mechanisms known in the art.

Figure 4:
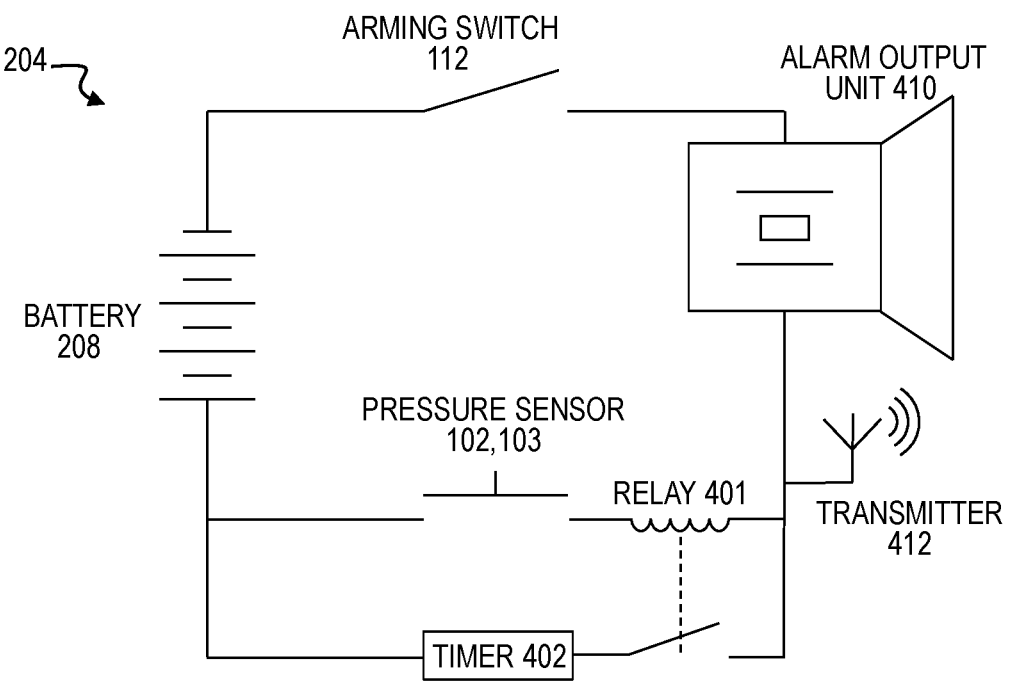
FIG. 4 is a schematic circuit diagram of system 100, according to some embodiments.

FIG. 4 is a schematic circuit diagram of alarm circuitry 204 used in system 101, according to some embodiments. In some embodiments, circuitry 204 includes a relay 401 and timer 402 that continues to activate the alarm output unit 410 for some number of seconds after the original circuit is incomplete (for example, 30 seconds after the dog releases the medication container system 100, but other durations can be used), to ensure that the medication owner hears it and can remove the container from the animal's access.

In some embodiments, circuitry 204 includes arming switch 112. In some embodiments, circuitry 204 delivers a mild shock to the animal's tongue through the conductive metal plates (pressure sensor) 102 and 103.

In some embodiments, circuitry 204 includes transmitter 412, configured to send a wireless alert message to the medication owner via at least one of a personal area network, a local area network, a wide area network, an internet connection to the cloud, or a cellular network.

In some embodiments, the alarm output unit 410 includes a flashing light bright enough to deter the animal.

In some embodiments, the present invention provides an apparatus for a medication container. This apparatus includes: a medication-container cover that includes: a pressure-sensitive sensor; a power supply; an alarm; and a circuit operatively coupled to the pressure-sensitive sensor and the power supply, wherein the circuit is wired to be completed when pressed by the force of an animal's bite or touched by an animal's tongue, and wherein the circuit is configured to activate the alarm.

In some embodiments, the pressure-sensitive sensor comprises a membrane that completes a circuit when pressed.

In some embodiments, the alarm includes an audio output alarm.

In some embodiments, the alarm includes a flashing light.

In some embodiments, the pressure-sensitive sensor includes two or more conductive metal sheets in layers around the side of the container.

Some embodiments further include spacers that separate said sheets or strips so that a normal human grip has insufficient force to complete the circuit.

In some embodiments, the interior metal sheet or strips form a tight friction fit with the pill bottle or medication container so that the medication-container cover is removable and reusable.

Some embodiments further include a bite-resistant switch to arm and disarm the circuit to prevent accidental loss of battery power when the device is not in use.

Some embodiments further include a relay and timer that continues to activate the alarm for a fixed time after the pressure-sensor circuit is incomplete.

Some embodiments further include a transmitter to alert the user, via the Internet of Things, when the alarm is activated.

Some embodiments further include an indicator light to confirm to the medication owner that the apparatus is activated and working.

Some embodiments further include the indicator light flashing intermittently to warn of low battery power.

Some embodiments further include the alarm chirping intermittently to warn of low battery power.

Some embodiments further include a hinge and clasp to allow access to change the batteries.

Some embodiments further include a battery access door in the outer conductive sheet.

Some embodiments further include small lateral gaps at the top and bottom edges of the outer conductive sheet, making the outer conductive sheet slightly smaller vertically than the inner conductive sheet, to increase the likelihood that both sheets will contact the animal's tongue and thereby complete the circuit.

Some embodiments further include a locking mechanism to attach the apparatus to the pill bottle or medication container to prevent accidental removal.

Some embodiments further include a circuit configured to deliver a mild electrical shock to the animal.

In some embodiments, the present invention provides a method for protecting animal health by covering a medication container with an alarm system. This method includes: detecting a pressure applied to the medication container covering; and based on the detected pressure, either activating an alarm or delivering a mild electrical shock to the animal, or both.

In some embodiments, the present invention provides an apparatus for a medication container. This apparatus includes: a medication container cover that includes: a pressure-sensitive sensor; a power supply; a circuit operatively coupled to the pressure-sensitive sensor and the power supply; wherein the circuit is wired to activate the circuit when pressed by the force of an animal's bite or touched by an animal's tongue, the circuit configured to deliver a mild electrical shock to the animal.

It will be apparent to anyone skilled in the art that the invention can be customized to fit many different standard sizes and shapes of medication containers.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," " "second," and "third," etc., are used merely as labels, and are not intended to impose numerical requirements on their objects.

What is claimed is:

1. An apparatus for a medication container, the apparatus comprising:
    a medication-container cover that includes:
        a pressure-sensitive sensor including an outer conductive membrane, an inner conductive membrane and a plurality of support members disposed between the outer and inner conductive membranes, wherein the outer conductive membrane is, concentrically disposed about and spaced apart from the inner conductive membrane;
        a power supply;
        an alarm; and
        a circuit operatively coupled to the outer conductive membrane, inner conductive membrane and the power supply; wherein the circuit is configured to activate when the outer conductive membrane is pressed by the force of an animal's bite, and wherein the circuit is configured to activate the alarm.

2. The apparatus of claim 1, wherein the outer conductive membrane is configured to displace inwardly and contact the inner conductive membrane to complete the circuit when pressed.

3. The apparatus of claim 1, wherein the alarm includes an audio output alarm.

4. The apparatus of claim 1, wherein the alarm includes a flashing light.

5. The apparatus of claim 1, wherein the outer conductive membrane and inner conductive membrane each comprise a conductive metal sheet or layer disposed around a side of the medication container.

6. The apparatus of claim 5, wherein the plurality of spacers separate the outer conductive membrane from the inner conductive membrane so that a normal human grip has insufficient force to complete the circuit.

7. The apparatus of claim 1, wherein the inner conductive membrane is configured to form a friction fit with the medication container.

8. The apparatus of claim 1, further including a bite-resistant switch to arm and disarm the circuit to prevent accidental loss of power from the power supply when the apparatus is not in use.

9. The apparatus of claim 1, further comprising a relay and timer that continues to activate the alarm for a fixed time after the circuit is activated.

10. The apparatus of claim 1, further including an indicator light to confirm to a human that the apparatus is activated and working.

11. The apparatus of claim 10, wherein the indicator light is configured to flash intermittently to warn of a low power state of the power supply.

12. The apparatus of claim 1, wherein the alarm is configured to chirp intermittently to warn of a low power state of the power supply.

13. The apparatus of claim 1, further including a hinge and clasp to allow access to change the power supply.

14. The apparatus of claim 1, wherein the power supply is a battery, and wherein the outer conductive membrane includes a battery access door.

15. The apparatus of claim 1, further comprising a locking mechanism to attach the apparatus to the medication container to prevent accidental removal.

16. The apparatus of claim 1, further comprising a circuit configured to deliver a mild electrical shock to the animal.

17. The apparatus of claim 1, further including a circuit configured to send a wireless alert message via at least one of a personal area network, a local area network, a wide area network, an internet connection to the cloud, or a cellular network.

18. A method for protecting animal health using a medication-container cover equipped with an alarm system, the method comprising:
    coupling the medication-container cover to a medication container, the medication-container cover including:
        a pressure-sensitive sensor including an outer conductive membrane, an inner conductive membrane and a plurality of support members disposed between the outer and inner conductive membranes, wherein the outer conductive membrane is disposed concentrically about and spaced apart from the inner conductive membrane;
        a power supply;
        an alarm; and
        a circuit operatively coupled to the outer conductive membrane, inner conductive membrane and the power supply;
    detecting a pressure applied to the medication container covering; and based on the detected pressure, either activating an alarm or delivering a mild electrical shock to the animal, or both.

19. An apparatus for a medication container, the apparatus comprising:
   a medication-container cover that includes:
      a pressure-sensitive sensor including an outer conductive membrane, an inner conductive membrane and a plurality of support members disposed between the outer and inner conductive membranes, wherein the outer conductive membrane is disposed concentrically about and spaced apart from the inner conductive membrane in a first operational state;
      a power supply; and
      a circuit operatively coupled to the outer conductive membrane, the inner conductive membrane and the power supply; wherein the circuit is configured to activate the circuit in a second operational state when pressed by the force of an animal's bite, the circuit configured to deliver a mild electrical shock to the animal when activated in the second operational state.

* * * * *